(12) United States Patent
Chao (10) Patent No.: US 10,493,044 B1
(45) Date of Patent: Dec. 3, 2019

(54) METHOD FOR TREATING DEVELOPMENTAL RETINAL VASCULAR DISORDER

(71) Applicant: Hsiao-Ming Chao, Taipei (TW)

(72) Inventor: Hsiao-Ming Chao, Taipei (TW)

( * ) Notice: Subject to any disclaimer, the term of this patent is extended or adjusted under 35 U.S.C. 154(b) by 0 days.

(21) Appl. No.: 15/992,126

(22) Filed: May 29, 2018

(51) Int. Cl.
*A61K 31/09* (2006.01)
*A61P 27/02* (2006.01)
*C07K 16/22* (2006.01)
*A61K 9/00* (2006.01)
*A61K 36/00* (2006.01)
*A61K 31/05* (2006.01)

(52) U.S. Cl.
CPC .............. *A61K 31/09* (2013.01); *A61P 27/02* (2018.01); *A61K 9/0048* (2013.01); *A61K 31/05* (2013.01); *A61K 36/00* (2013.01); *C07K 16/22* (2013.01)

(58) Field of Classification Search
CPC ................................ A61K 36/00; A61K 31/05
USPC .......................................... 424/725; 514/736
See application file for complete search history.

(56) References Cited

FOREIGN PATENT DOCUMENTS

| CN | 103494794 A | * | 1/2014 |
| CN | 103920151 A | * | 7/2014 |

OTHER PUBLICATIONS

English Translation of CN 103920151 A (2014) and an English-translated abstract.*
English Translation of CN 103494794 A (Ji et al.) (2014) and an English-translation abstract.*

* cited by examiner

*Primary Examiner* — Kevin E Weddington
(74) *Attorney, Agent, or Firm* — Hannah Tien (57) ABSTRACT

A method for treating a subject suffering from a developmental retinal vascular disorder by administering to the subject a composition which has a therapeutically effective amount of a dendrobium nobile lindley (DNL).

8 Claims, 9 Drawing Sheets
(4 of 9 Drawing Sheet(s) Filed in Color)

METHOD FOR TREATING DEVELOPMENTAL RETINAL VASCULAR DISORDER

FIELD OF THE INVENTION

The present invention relates to a method for treating a subject suffering from a developmental retinal vascular disorder, comprising administering to the subject a composition comprising a therapeutically effective amount of dendrobium nobile lindley (DNL).

BACKGROUND OF THE INVENTION

Defects in vasculogenesis (early retinal vessel development) seem to be mediated through the Norrin-dependent Wnt signaling pathway. Norrin/Frizzled-4 signaling plays a crucial role in vasculogenesis such as in Norrie disease (ND) and familial exudative vitreoretinopathy (FEVR), which might eventually progress into retinal ischemia and neovascularization (NV; angiogenesis). In addition to ND and FEVR, there are other developmental retinal vascular disorders, namely Coats disease and persistent hyperplastic primary vitreous (PHPV), which share similar fundus images, namely peripheral retinal avascularization and subretinal exudation. As described above, these vitreoretinopathies may also cause retinal ischemia producing a similar threat to patients' vision, although they are not as common as other retinal ischemic disorders, such as central/branch retinal artery occlusion (CRAO/BRAO), central/branch retinal vein occlusion (CRVO/BRVO), glaucoma, diabetic retinopathy (DR) and neovascular age related macular generation (nvAMD). The persistent hypoxia is assumed to be one of the major driving forces of progression of these developmental retinal vascular disorders such as ND.

RGCs and amacrine cells in the inner retina are susceptible to ischemia/reperfusion (I/R). Moreover, vimentin/glial fibrillary acidic protein (GFAP) immunolabeling of Millers is elevated after ischemia; which is associated with RGC number reduction. Overexpression of vascular endothelium growth factor (VEGF), hypoxia inducible factor-1α (HIF-1α), pyruvate kinase M2 (PKM2) and retinoblastoma-binding protein 2 (RBP2) are known to occur concomitantly in the ischemic retina, and further abnormal NV (late neovessel formation) may lead to visual impairments due to edema and hemorrhage. Upregulation of HIF-1α and VEGF can also be observed in the Norrin depleted retina. In addition to VEGF, placental growth factor (PLGF) has been reported to be increased in defined ischemic disorders of the retina/choroid vasculature; thus, downregulation of this factor can be utilized as a biomarker for visual functional outcome and treatment.

DNL (a member of the Orchidae family) is a "vision improving" herb. DNL has also been used as a tonic drug and found to have antipyretic/anti-inflammatory effects and anti-angiogenic (e.g. anti-VEGF/HIF-1α) properties. DNL has several active ingredients with various action mechanisms, including alkaloids (TNFR1 overexpression via inhibiting the p-p38 MAPK and NF-κB pathway), flavonal glycosides (α-glucosidase inhibition), SG-168 and polysaccharides (antioxidation). Furthermore, an anti-angiogenic or anti-oxidative moscatilin is an active component (bibenzyl) of DNL, which might have known (anti-VEGF/HIF-1α, OH radical scavenger, anti-inflammation and anti-apoptosis) and unknown action mechanisms different from those of the above-mentioned components.

SUMMARY OF THE INVENTION

The present invention relates to a method for treating a subject suffering from a developmental retinal vascular disorder, comprising administering to the subject a composition comprising a therapeutically effective amount of dendrobium nobile lindley (DNL).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 (a-e) shows the cell viability study of the effects of moscatilin on retinal ganglion cell-5 (RGC-5) cells subjected to oxygen glucose deprivation (OGD) using light microscopy. After pre-administration of dimethyl sulfoxide (DMSO) (vehicle) and followed by OGD (DMSO+OGD), the cells are found to be less numerous and some are deformed (as indicated by arrows) as compared to the normal control group (cells cultured in DMEM and pre-administration of DMSO; DMSO+DMEM). These OGD-induced alterations are mitigated by pre-administration of moscatilin at 1 hour pre-OGD (Mos; Pre-OGD 0.1 μM Mos). f: The effects of moscatilin on cells subjected to OGD underwent MTT assay are quantitatively analyzed. ** indicates a significant difference (P<0.01) between the control group (DMSO+DMEM) and the "DMSO+OGD" group. † indicates a significant difference (P=0.04) between the "DMSO+OGD" group and the "Pre-OGD 0.1 μM Mos" group. Results are presented as means±S.E.M. (n=6). Scale=50 μm. DMSO+DMEM (control): DMSO in DMEM; DMSO+OGD: OGD and treatment with DMSO at 1 hr pre-OGD; Pre-OGD Mos 0.1 μM: OGD and treatment with 0.1 μM moscatilin at 1 hr pre-OGD; During OGD Mos 0.1 μM: OGD and treatment with 0.1 μM moscatilin during OGD; and Post-OGD Mos 0.1 μM OGD and treatment with 0.1 μM moscatilin at 1 hr post-OGD.

FIG. 2 shows the effect of moscatilin (Mos) on the protein levels of norrie disease protein (NDP) relative to β-actin. Top: a series of representative immunoblotting images. Bottom: a bar chart. The expression level of NDP:β-actin protein in the normal control group (DMSO+DMEM: RGC-5 cells cultured in DMEM and pre-administration of DMSO) is adjusted to 100%. ** indicates a significant difference (P<0.01) between the "DMSO+DMEM" group and the "DMSO+OGD" group. † indicates a significant difference (P=0.048) between the "DMSO+OGD" group and the "Pre-OGD 0.1 μM Mos" group (0.1 μM moscatilin given 1 hour pre-OGD). The results are presented as means±S.E.M. (n=3). OGD: oxygen glucose deprivation; and RGC: retinal ganglion cell. DMSO+DMEM: DMSO in DMEM; DMSO+OGD: OGD and treatment with DMSO at 1 hr pre-OGD; Pre-OGD Mos 0.1 μM: OGD and treatment with 0.1 μM moscatilin at 1 hr pre-OGD; During OGD Mos 0.1 μM: OGD and treatment with 0.1 μM moscatilin during OGD; and Post-OGD Mos 0.1 μM OGD and treatment with 0.1 μM moscatilin at 1 hr post-OGD.

FIG. 3 shows the electroretinogram (ERG) analysis (a and b). Compared to the control retina (Sham), there is a drastic decrease in the ERG b-wave amplitudes after high intraocular pressure (HIOP)-induced retinal ischemia plus reperfusion (I/R) and pre-administration (see a) or post-administration (see b) of the vehicle. This decrease is dose-dependently counteracted by pre-ischemia administration of dendrobium nobile lindley (DNL) (DNL1.0+I/R; DNL0.5+I/R; a) or post-ischemia administration of DNL (I/R+DNL1.0; b). c: Compared to the normal control (sham), a significant (; P<0.01) decrease in the ERG b-wave ratio occurs in the "Vehicle+I/R" group after retinal I/R. A significant (††; P<0.01) counteraction of this ischemia-induced reduction is dose-responsive and obtained when a high dose (DNL1.0+I/R) and a low dose (DNL0.5+I/R) of DNL is pre-administered. d: ERG b-wave amplitude is found to be significantly (; P<0.01) reduced on day 1, 3, 5 or 7 after retinal I/R and post-ischemia administration of the vehicle. A significant (†/††; P<0.05/0.01) alleviation of this reduction in ERG b-wave amplitude is achieved by post-administration of DNL (I/R+DNL1.0). The results are presented as means±S.E.M. (n=10-12). Sham (n=12; control): sham procedure; Vehicle+I/R (n=12): Pre-ischemic treatment with the vehicle followed by I/R; DNL0.5+I/R (n=12): Pre-ischemic treatment with DNL0.5 followed by I/R; DNL1.0+I/R (n=12): Pre-ischemic treatment with DNL1.0 followed by I/R; I/R+Vehicle D7: I/R followed by post-ischemic treatment with the vehicle on day 7; I/R+DNL1.0: I/R followed by post-ischemic treatment with DNL1.0 on day 7; I/R+Vehicle (n=10): I/R followed by post-ischemic treatment with the vehicle; I/R+DNL1.0 (n=10): I/R followed by post-ischemic treatment with DNL1.0. Pre-ischemia: procedure before ischemia; Post-ischemia D1: 1 day after ischemia; Post-ischemia D3: 3 days after ischemia; Post-ischemia D5: 5 days after ischemia; Post-ischemia D7: 7 days after ischemia.

FIG. 4 shows the analysis of the thickness of the whole or inner retina labeled with cresyl violet. a, b and e respectively show a retina that receives the sham procedure (Sham), or I/R and pre-administration (see b)/post-administration of the vehicle (see e). c, d and f are retinas that undergo I/R and pre-administration of 0.5 g/kg/day (c, DNL0.5+I/R), or 1.0 g/kg/day (d, DNL1.0+I/R), or post-administration of 1.0 g/kg/day (f, I/R+DNL1.0) of DNL. The thickness of the whole or inner retina obtained from sections of equal eccentricity are morphometrically analyzed (g, h). The results are presented as means±S.E.M. (n=10-12). ** represents a significant difference (P<0.01) from the Sham retina. † or †† represents a significant difference (P<0.05 or P<0.01) from the Vehicle+I/R or I/R+Vehicle. ONL: outer nuclear layer; OPL: outer plexiform layer; INL: inner nuclear layer; IPL: inner plexiform layer; GCL: ganglion cell layer. Scale bar=50 µm.

FIG. 5 shows fluorogold labeling. The microscopic images show the retinal ganglion cell (RGC) density after the sham procedure (a, Sham), or after ischemia followed by reperfusion (I/R) plus pre-ischemia administration of the vehicle (b, Vehicle+I/R) or pre-/post-ischemia administration of DNL at 1.0 g/kg/day (c, DNL1.0+I/R; d, I/R+DNL1.0). The RGC density is quantitatively analyzed (e). As indicated by each bar, the results are means±S.EM. (n=4). ** indicates a significant difference from the sham retina (P<0.01; Sham vs. Vehicle+I/R); †† or † indicates a significant difference from the Vehicle+I/R (P<0.01 or P<0.05; Vehicle+I/R vs. DNL1.0+I/R or I/R+DNL1.0). Scale bars=50 µm.

FIG. 6 shows choline acetyltransferase (ChAT, red) immunohistochemical studies. a shows a retina that undergoes the sham procedure (Sham); cell nuclei are counterstained with 4,6-diamidine-2-phenylindole dihydrochloride (DAPI, blue). Amacrine cell bodies (Sham; short arrows) can be seen in the INL and GCL and their neuronal processes (long arrow) display a two-band pattern in the IPL. b and e show retinas that undergo I/R together with pre-/post-administration of the vehicle (Vehicle+I/R or I/R+Vehicle); furthermore, a considerable reduction in the IPL immunoreactivity can be seen together with a great reduction in the number of amacrine cell bodies. c, d and f show sectioned retinas that have received I/R and pre-administration of 0.5 g/kg/day (c, DNL0.5+I/R), or 1.0 g/kg/day of DNL (d, DNL1.0+I/R), or that has received I/R and post-administration of 1.0 g/kg/day of DNL (f, I/R+DNL1.0). In these groups, the ischemia-induced changes can be obviously and dose-dependently mitigated when the ischemic retinas receive pre-administration of 0.5 and 1.0 g/Kg/day of DNL. Post-administration of 1.0 g/Kg/day of DNL also obviously mitigates these ischemia-induced changes. Scale bar=50 µm.

FIG. 7 shows vimentin immunohistochemistry (see b). After the sham procedure (Sham), anti-vimentin (green) immunoreactivity can be seen in Müller cells' end feet (arrow heads; see also c and f) within the ganglion cell layer (GCL), their processes are also immunolabeled in the IPL, INL and ONL (arrows; see also c and f). c and f: Compared to the sham retina, there is a considerable enhancement of anti-vimentin immunolabeling after ischemia and pre-administration or post-administration of the vehicle (Vehicle+I/R or I/R+Vehicle). d, e and g: This enhancement is obviously counteracted by pre-administration of 0.5 g/kg/day (DNL0.5+I/R), or 1 g/kg/day of DNL (DNL1.0+I/R), or post-1 administration of 1 g/kg/day of DNL (I/R+DNL1.0). h-n show glial fibrillary acidic protein (GFAP) immunohistochemical studies. After the sham procedure (Sham; i), the Müller cells display GFAP immunoreactivity at their end feet within the GCL (arrow heads; see also j and in), and at their processes in the IPL (arrows; see also j and in), INL and ONL. Compared to the Sham retina, anti-GFAP immunolabeling is enhanced after ischemia and pre-/post-administration of the vehicle (Vehicle+I/R, j; I/R+Vehicle, in). This enhancement is mitigated by pre-administration of 0.5 g/kg/day (DNL0.5+I/R; k) or 1 g/kg/day of DNL (DNL1.0+I/R; l), or post-administration of 1 g/kg/day of DNL (I/R+DNL1.0; n). a and h: DAPI (blue) is used to counterstain cell nuclei in the sham retina. Scale bar=25 µm.

FIG. 8 shows a western blot analysis, image a1 shows the expression levels of β-actin, HIF-1α, VEGF, pyruvate kinase M2 (PKM2) and retinoblastoma binding protein 2 (RBP2). Lane 1 or 2 is the sham retina subjected to the sham procedure (Sham), or the ischemic retina pre-administered with the vehicle (Vehicle+I/R), respectively. Lane 3 shows a retina that receives ischemia together with pre-ischemia administration of 1 g/kg/day DNL (DNL1.0+I/R). Lanes 4-6 show retinas that undergo ischemia together with pre-ischemia administration of 10 µM/5 µl JIB-04 (RBP2 inhibitor), 4 µM/5 µl shikonin (PKM2 inhibitor), or 125 µg/5 µl avastin (anti-VEGF), respectively. Each bar in diagram a2 represents the ratio of RBP2, PKM2, VEGF and HIF-1α to β-actin.  indicates a significant (P<0.01) difference between the Sham retina and the ischemic retina pre-administered with the vehicle (Vehicle+I/R). † or †† indicates significant (P<0.05 or P<0.01) difference between the "Vehicle+I/R" group and the ischemic retina pre-administered with DNL1.0, JIB-04, shikonin or avastin. The results are presented as means±S.E.M. (n=4-10). b shows the results of the ELISA assay. The concentration of placental growth factor (PLGF) is measured in retinas of various groups, namely Sham, Vehicle+I/R, DNL1.0+I/R or Eylea+I/R. Rats that receive I/R plus pre-ischemia administration of 200 µg/5 µl Eylea are defined as the "Eylea+I/R" group.  indicates a significant difference (P<0.01) between the Sham retina and Vehicle+I/R. † or †† indicates significant (P<0.05 or P<0.01) difference between Vehicle+I/R and DNL1.0+I/R or Eylea+I/R. Results are presented as means±S.E.M. (n=4).

FIG. 9 shows the pathway analysis for DNL/moscatilin treating ischemia. NDP: Norrie disease protein; PKM2: pyruvate kinase M2; RBP2: retinoblastoma binding protein 2; HIF-1α: hypoxia inducible factor; VEGF-A: vascular endothelium growth factor-A; VEGF-A: vascular endothelium growth factor-B; PLGF: placental growth factor.

DETAILED DESCRIPTION OF THE INVENTION

The present invention has demonstrated various ischemic/hypoxic (OGD) alterations that occur in the retina or retinal cells by the electroretinography, the immunohistochemistry (RGCs, amacrines, Millers), the histopathology (retinal thickness), the cell viability and protein measurement assay (PLGF, HIF-1α, VEGF-A, PKM2, RBP2 and NDP). The present prevention finds that the protein levels of HIF-1α, VEGF, PKM2 and RBP2 are significantly upregulated in the ischemic retinas but these significantly upregulated proteins are significantly reduced by administration of DNL. The ischemia-induced elevation of PLGF is also significantly blunted when ischemic retinas are pre-administered with the VEGF trap/anti-PLGF Eylea. This is also the case to the effect of 1.0 g/Kg/day of DNL. Of novelty and clinical significance, DNL may thus possess anti-angiogenesis/VEGF (PLGF) trapping effect. Not inconsistent with previous reports, DNL's bibenzyl component moscatilin has been also proved to be an anti-angiogenetic agent through its inhibition effects on HIF-1α and VEGF.

The ischemia may be strongly related to developmental retinal vasculopathy such as FEVR or ND. The anti-VEGF antibodies have been used to effectively clear ocular hemorrhage and macular edema; disappointingly, poor visual results still occur in some patients. The norrin-dependent Wnt-signaling pathway is involved in both early normal development of retinal vessels and late progression of defined developmental retinal vascular diseases. The latter condition may further aggravate ischemia/hypoxia and form NV. Consistently, NDP (norrin) seems to protect the eye from abnormal angiogenesis and retinopathy by modulating the norrin-dependent Wnt signaling pathway. Moreover, overexpression of NDP has been shown to protect photoreceptors and RGCs from cell death via activation of the norrin-dependent Wnt signaling pathway. The present invention demonstrates that hypoxia (OGD) leads to a significant decrease in the NDP level and cell viability. Furthermore, significant counteraction in the OGD induced reduction in NDP level and cultured cell number has implied that moscatilin (0.1 μM), a bibenzyl ingredient of DNL, is able to significantly alleviate hypoxic/ischemic-like (OGD) injury. Thus, the present invention demonstrates that DNL and/or moscatillin is able to activate the NDP (norrin)-dependent Wnt signaling pathway and thus to provide neuroprotection against retina ischemia, presumably, by inhibiting VEGF-A/PLGF and upregulating NDP.

In addition, after ischemic insult and administration of a vehicle, the inner retinal thickness, the number of RGCs and the ChAT immunoreactivity of amacrine cells are significantly or obviously decreased. Importantly, the present invention also confirms that these ischemia induced changes are significantly and obviously blunted by pre- and/or post-administration of a high dose of DNL (at 1 g/kg/day). Moreover, in the ischemic retinas with pre-/post-administration of the vehicle, vimentin/GFAP immunolabeling overexpression parallel the decrease in b-wave. It is of clinical importance that the present results have also shown that these ischemic alterations are significantly or obviously counteracted by pre-/post-administration of DNL at 1 g/kg/day.

Figure 9:
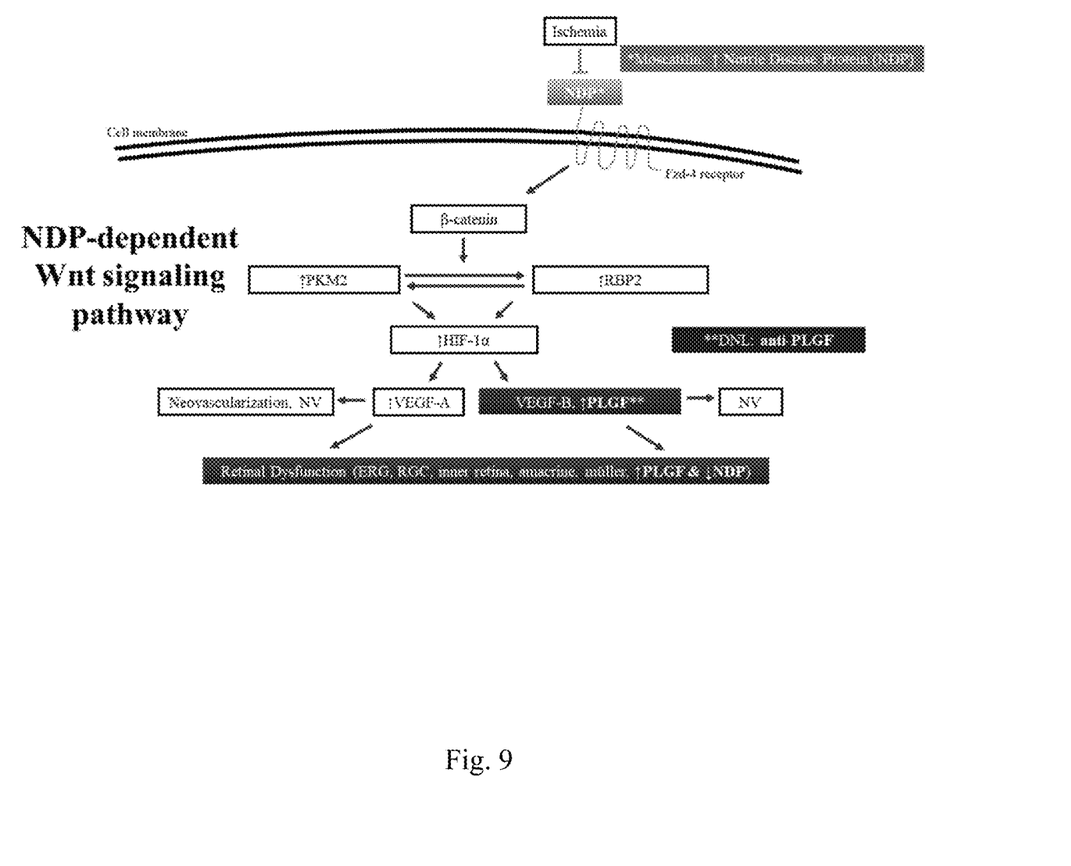

The results of the present invention demonstrate that ischemia/hypoxia (ischemia-mimetic OGD) significantly and obviously affects the retina electrophysiologically, morphometrically, immunohistochemically in terms of the retinal molecular biology/cellular viability. Of clinical importance, all these changes, which follow ischemia/OGD, are effectively attenuated by pre-treatment and/or post-treatment with DNL or its bibenzyl component moscatilin. The present invention considers that these protective mechanisms are performed by suppressing the upregulation of HIF-1α, VEGF-A, PKM2, RBP2, and, above all, PLGF, as well as, by upregulating the level of NDP (see FIG. 9).

Taken together, DNL and/or moscatilin is able to protect against or even prevent defined retinal ischemic/ischemic-like alterations through inhibition of the PLGF and, probably, the upregulation of NDP. DNL treatment (and/or moscatilin) may be an useful way of providing complementary access that allows the prevention and/or management of patients with developmental vascular disorders that may progress due to persistent ischemia/hypoxia.

Figure 2:
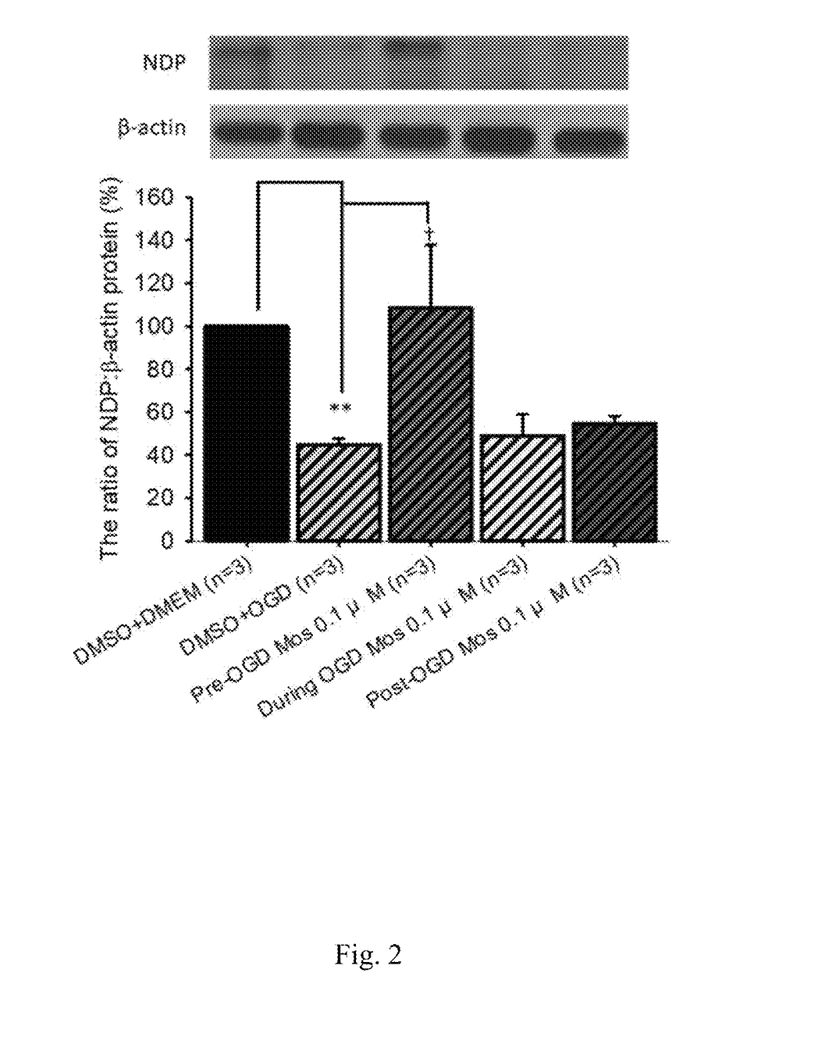

The present invention uses electroretinograms (b-wave changes on müller cells and bipolar cells), immunohistochemistry (fluorescence immunolabeled retinal ganglion cells (RGC), ChAT-immunolabeled amacrine cell, vimentin/GFAP stained müller cells), histopathology (retinal thickness measurement), and/or western blotting (HIF-1α, VEGF, PKM2 and RBP2) to observe various ischemic changes in rat retinas. Importantly, the ischemic retinas with pre-/post-administration of DNL can significantly modulate all of these defined ischemic related features. Most importantly, PLGF is upregulated in the retinal ischemia/ischemi-like (OGD) conditions (FIG. 8), and the protein concentration of NDP is downregulated (FIG. 2). However, these changes are counteracted by treatment with DNL/moscatilin. Of clinical importance, DNL can prevent or protect the defined retinal ischemia/ischemic changes by downregulating PLGF and upregulating NDP. Thus, DNL/moscatillin provide an alternative way to bring about prevention or management of patients with persistent hypoxia/ischemia associated progression of developmental vascular disorders such as ND by downregulating the level of PLGF and upregulating the concentration of NDP.

The term "a" or "an" as used herein is to describe elements and ingredients of the present invention. The term is used only for convenience and providing the basic concepts of the present invention. Furthermore, the description should be understood as comprising one or at least one, and unless otherwise explicitly indicated by the context, singular terms include pluralities and plural terms include the singular. When used in conjunction with the word "comprising" in a claim, the term "a" or "an" may mean one or more than one.

The term "or" as used herein may mean "and/or."

The present invention provides a method for treating a subject suffering from a developmental retinal vascular disorder, comprising administering to the subject a composition comprising a therapeutically effective amount of dendrobium nobile lindley (DNL).

In one embodiment, the dendrobium nobile lindley (DNL) comprises bibenzyls, glycosides and polysaccharides. In a preferred embodiment, the DNL comprises bibenzyls. In a more preferred embodiment, the bibenzyls comprises moscatilin.

In another embodiment, the structural formula of the moscatilin is:

In one embodiment, the treatment of developmental retinal vascular disorder is achieved by improving the defects in the development of the retinal vessels. The development of the retinal vessels is divided into two phases: (1) vasculogenesis: it begins at around 18 weeks gestation (WG) and is completed by 38-40 WG. The vessels are organised into a network of vascular plexuses, which form by a combination of vasculogenesis and angiogenesis. Vasculogenesis is the process of vessel development de novo from endothelial precursor cells that coalesce into cords and then form a lumen; (2) angiogenesis: the blood vessels are formed by sprouting from pre-existing vessels. It is believed that the vasculogenesis forms most of the primary retinal vascular plexus of the developing human retina, while the angiogenesis forms the remaining capillary layers around the fovea and in the deeper and peripheral retina. In a preferred embodiment, the DNL or the moscatilin improves the defects in the vasculogenesis to treat the developmental retinal vascular disorder.

As used herein, the term "treating" refers to therapeutic treatments, wherein the subject is to reverse, alleviate, ameliorate, inhibit, slow down or stop the progression or severity of a condition associated with a developmental retinal vascular disorder. The term "treating" includes, but is not limited to, a preventive treatment and/or a therapeutic treatment.

In another embodiment, the developmental retinal vascular disorder comprises persistent hyperplastic primary vitreous (PHPV), norrie disease (ND), familial exudative vitreoretinopathy (FEVR), and Coats disease. In a preferred embodiment, the developmental retinal vascular disorder comprises norrie disease and familial exudative vitreoretinopathy. In a preferred embodiment, the developmental retinal vascular disorder is norrie disease.

Because the developmental retinal vascular disorder is a disease of the abnormal development of the retinal vessels, it causes retinal ischemia and visual impairments of a patient. In another embodiment, the symptoms of the developmental retinal vascular disorder comprise an abnormal development of retinal vessels, retinal ischemia and visual impairments.

Because the developmental retinal vascular disorder causes the retinal ischemia, the retinal ischemia further causes a retinal ischemic damage. In one embodiment, the retinal ischemic damage comprises a decrease in the retinal thickness, a decrease in the number of retinal ganglion cells (RGCs), and an increase in the level of the related factors (e.g., hypoxia-inducible factor (HIF), retinoblastoma-binding protein 2 (RBP2), pyruvate kinase M2 (PKM2) and vascular endothelial growth factor (VEGF)). In another embodiment, the DNL or the moscatilin treats the retinal ischemic damages caused by the developmental retinal vascular disorder.

The retinal ischemic damage causes a decrease in the retinal thickness, but the administration of the DNL or the moscatilin can prevent the retinal thickness from decreasing, i.e., the DNL or the moscatilin can treat or increase the retinal thickness. In one embodiment, the DNL or the moscatilin treats the degree of decrease in the retinal thickness caused by the developmental retinal vascular disorder.

This developmental retinal vascular disorder causes a retinal ischemic damage and further causes a decrease in the number of the retinal ganglion cells (RGCs), but the administration of the DNL or the moscatilin increases the number of the RGCs or prevents the RGCs from cell death, thereby treating the ischemic retinal damage caused by the developmental retinal vascular disorder. In one embodiment, the DNL or the moscatilin increases the number of retinal ganglion cells (RGCs).

In addition, the developmental retinal vascular disease causes the retinal ischemic damage and increases the level of hypoxia-inducible factor (HIF), retinoblastoma-binding protein 2 (RBP2), pyruvate kinase M2 (PKM2) and vascular endothelium growth factor (VEGF) in the retina, but the administration of the DNL or the moscatilin is able to reduce the level of the above factors to treat the retinal ischemic damage caused by the developmental retinal vascular disorder. In one embodiment, the DNL or the moscatilin decreases the level of HIF-1α, RBP2, PKM2 and VEGF.

The developmental retinal vascular disorder is able to induce angiogenesis. Therefore, in another embodiment, the DNL or the moscatilin traps the VEGF for anti-angiogenesis.

As used herein, the term "level" includes, but is not limited to, the level of DNA, RNA or the protein.

The retinal ischemic damage caused by the developmental retinal vascular disorder upregulates the level of placenta growth factor (PLGF) and downregulates the level of norrie disease protein (NDP). The administration of the DNL or the moscatilin can downregulate the level of the PLGF and upregulate the level of the NDP to treat an ischemic/hypoxic injury in the retina induced by the developmental retinal vascular disorder. The NDP is able to protect the eye from abnormal development of retinal vessels and the retinal ischemic injury by modulating the norrin-dependent Wnt signaling pathway. In one embodiment, the DNL or the moscatilin downregulates the level of PLGF and upregulates the level of NDP. In a preferred embodiment, the DNL or the moscatilin upregulates the level of NDP for modulating the Norrin-dependent Wnt signaling pathway to improve the abnormal development of the retinal vessels. In a more preferred embodiment, the DNL or the moscatilin upregulates the level of NDP for modulating the Norrin-dependent Wnt signaling pathway to improve the retinal ischemia.

The term "therapeutically effective amount" used herein is a therapeutic dose which can prevent, decrease, stop or reverse a symptom developed in a subject under specific conditions, or partially, completely alleviates symptoms already exist under specific conditions when the subject begins receiving the treatment.

In one embodiment, the therapeutically effective amount of the DNL ranges from 0.01 g/kg to 100 g/kg. In a preferred embodiment, the therapeutically effective amount of the DNL ranges from 0.1 g/kg to 50 g/kg. In a more preferred embodiment, the therapeutically effective amount of the DNL ranges from 0.5 g/kg to 10 g/kg. In another embodiment, the therapeutically effective amount of the DNL ranges from 0.1 g/kg to 5 g/kg.

In one embodiment, the therapeutically effective amount of the moscatilin ranges from 0.01 g/kg to 100 g/kg. In a preferred embodiment, the therapeutically effective amount of the moscatilin ranges from 0.1 g/kg to 50 g/kg. In a more preferred embodiment, the therapeutically effective amount of the moscatilin ranges from 0.5 g/kg to 10 g/kg. In another embodiment, the therapeutically effective amount of the moscatilin ranges from 0.1 g/kg to 5 g/kg.

In one embodiment, the therapeutically effective amount is administered in a single dose per day. In a preferred embodiments, the therapeutically effective amount is administered in two or more doses per day.

The composition of the present invention may be administered on a routine schedule. As used herein a routine schedule refers to a predetermined designated period of time. The routine schedule may encompass periods of time which are identical or which differ in length, as long as the schedule is predetermined. For instance, the routine schedule may involve administration one dose a day, every day, every two days, every three days, every four days, every five days, every six days, a weekly basis, a monthly basis or any set number of days or weeks there-between. Alternatively, the predetermined routine schedule may involve administration on a one daily basis for the first week, followed by a daily basis for several months, etc. In other embodiments, the present invention provides that the drug(s) may be taken orally and that the timing of which is or is not dependent upon food intake. Thus, for example, the drug can be taken every morning and/or every evening, regardless of when the subject has eaten or will eat.

The composition of the present invention further comprises a pharmaceutically acceptable carrier which may be administered to a subject through a number of different routes known in the art. In one embodiment, the composition (comprising the DNL or the moscatilin) and a pharmaceutically acceptable carrier are administered externally, intravenously, subcutaneously, topically, orally or by muscle or inhalation. The composition will be delivered to target sites by the digestive system or the circulatory system. In a preferred embodiment, the route of the administration for the composition is oral administration.

In another embodiment, the subject is an animal, preferably a mammal, more preferably a human.

As used herein, the term "pharmaceutically acceptable carrier" is determined in part by the particular composition being administered, as well as by the particular method used to administer the composition. Carrier can include aqueous isotonic sterile injection solutions, which can contain antioxidants, buffers, bacteriostatic agents, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions. The term "pharmaceutically acceptable" refers to compounds and compositions which can be administered to mammals without undue toxicity.

The composition (including the DNL or the moscatilin) and pharmaceutically acceptable carrier may be formulated via sterile aqueous solutions or dispersions, aqueous suspensions, oil emulsions, water in oil-in-oil emulsions, specific emulsification liquids, long residence emulsifiers, viscous emulsions, microemulsions, nanoemulsions, liposomes, microparticles, microspheres, nanospheres, nanoparticles, micromercury, and several sustainable releases of natural or synthetic polymers. The pharmaceutically acceptable carrier and the DNL (or the moscatilin) can also be prepared as aerosols, tablets, pills, capsules, sterile powders, suppositories, lotions, creams, ointments, pastes, gels, hydrogels, sustained delivery devices, or other formulations which may be used for drug delivery.

Therefore, the composition provided by the present invention (comprising the DNL or the moscatilin) is able to treat the developmental retinal vascular disorders, and the composition further repairs or treats the abnormal development of the blood vessels or the defects of the retinal vessels. Because the abnormal development of the retinal vessels cause the retinal ischemia, the composition of the present invention can further ameliorate the adverse effects or the damage of ischemia/hypoxia on the retina. In other words, the composition protects the retina from ischemic/hypoxic injury.

Examples

The embodiment of the present invention could be implemented with different content and is not limited to the examples described in the following text. The following examples are merely representative of various aspects and features of the present invention.

Methods

Chemicals and Drug Administration

DNL was purchased from the Ko Da Company (Taipei, Taiwan) and dissolved in $ddH_2O$. For the electrophysiological, immuohistochemical and molecular biological studies, drug administration was carried out for seven days and involved various groups, namely a post-ischemia administration (daily high dose of DNL at 1 g/kg/day, I/R+DNL1.0), or pre-ischemia administration (daily high dose of DNL, DNL1.0+I/R; low dose of DNL at 0.5 g/kg/day, DNL0.5+I/R). The rats in the vehicle group that were subjected to ischemia were either post-administered (I/R+Vehicle) or pre-administered with a similar volume of vehicle (Vehicle+I/R) as the DNL group.

As compared with the Sham, Vehicle+I/R or DNL1.0+I/R group, the ischemic eyes of other groups received intravitreal injections using a 30-gauge needle connected to a 25 µl syringe after the pupil was dilated with 1% tropicamide and 2.5% phenylephrine. Specifically, the ischemic eyes received 1 day pre-ischemia intravitreal administrations of various inhibitors/antibodies, namely 10 µM/5 µl JIB-04 (Sigma-Aldrich), 4 µM/5 µl Shikonin (S7576; Sigma-Aldrich), 125 µg/5 µl Avastin (Hoffmann-La Roche), or 200 µg/5 µl Eylea (Regeneron Pharmaceuticals Inc.). One day after retinal I/R and administration of relevant compounds or after a sham procedure, the animals were sacrificed. Retinal samples were collected in order to measure the protein levels of HIF-1µ, RBP2, PKM2, VEGF-A and PLGF by the western blot assay or ELISA.

Moscatilin was purchased from EMMX Biotechnology (EN10271, CA, USA) and dissolved in DMSO (vehicle). In previous reports, higher concentrations of moscatilin (1.25-20 µM) dose- and time-dependently reduced cell viability with IC50 at 7.0 and 6.7 µM for 24 h in two cell lines, respectively; thus, 0.1 µM was presently selected to evaluate its protective effect against OGD. Moscatilin (0.1 µM) was administered at 1 hour pre-OGD, during OGD, or at 1 hour post-OGD. Its therapeutic effects were evaluated by MTT and Western blotting assays.

In Vitro Studies

Oxygen Glucose Deprivation and Cell Treatment

The RCG-5 cell lines were not transformed rat RGCs but, rather, mouse retinal neuronal precursors. OGDs were defined as cells that were maintained in glucose-free DMEM (Thermo Fisher Scientific Inc.) at 37° C. under the hypoxic (ischemic-like) conditions, namely 1% $O_2$ (monitored by an analyzer; Penguin Incubator: control range 1-89%; Astec Company, Kukuoka, Japan), 94% $N_2$ and 5% $CO_2$. There were different groups, consisting of cells that received (i) DMSO in DMEM (control cells; DMSO+DMEM), (ii) DMSO followed by OGD (DMSO+OGD), (iii) OGD and administration of moscatilin (0.1 µM in DMEM) at 1 hour pre-OGD (Pre-OGD Mos 0.1 µM), (iv) during OGD (During OGD Mos 0.1 µM), or (v) at 1 hour post-OGD (Post-OGD Mos 0.1 µM). At the end of the 1 day OGD period, the cell cultures were returned to fresh DMEM for another 24 h. The MTT (viability) and the Western blotting assays (NDP) were then performed.

MTT Cell Viability Assay

Mitochondria NADPH dependent oxidoreductases were capable of reducing MTT to form formazan. Therefore, an increase in the amount of dark purple formazan corresponded to greater cell viability. MTT (0.5 mg/mL; Sigma-Aldrich) was added and allowed to react for 3 hr at 37° C. to the 96-well plates containing the original 100 µL of cells. The reduced MTT was then solubilized by adding 100 µL DMSO. After agitation of the plates, the OD of the solubilized formazan was measured using an ELISA reader (Synergy H1 Multi-Mode Reader BioTek Instruments) at 562 nm. Cell viability was expressed as OD values relative to the control (100%).

In Vivo Studies

Animals

The present invention used six-week-old Wistar rats (250-300 g; BioLasco, Taipei) for the following experiments.

Establishing Retinal Ischemia

Anesthesia and euthanasia. An intraperitoneal injection (i.p.) of 100 mg/kg ketamine (Pfizer) and 5 mg/kg xylazine (Sigma-Aldrich) was used to anesthetize the animals. Furthermore, at least 140 mg/kg sodium pentobarbital (SCI Pharmtech) was intraperitoneally given to humanely kill the animals.

Ischemia induction. Each rat was anesthetized with the above anesthetics and placed in a stereotaxic frame. The anterior chamber of one eye was cannulated using a 30-gauge needle linked to an elevated 0.9% saline reservoir; this caused an increase in IOP to 120 mmHg for 1 hour. A whitening of the retina indicated the build-up of ischemic injury. A sham version of the above-mentioned ischemia induction procedure, but without the elevation of the saline bottle connected to the rat's eye, was carried out as a control. Animals were placed on a heating pad at 37° C. and kept normothermic during ischemia & the following 3-hour reperfusion.

Flash ERG Measurements

Flash ERG were recorded from all the animals before the sham procedure or I/R (day 0), and one day after the sham procedure or I/R and pre-administration of the defined drugs. In the post-administration group, ERG data were recorded for all the animals pre-ischemia (day 0), and post-ischemia (post-ischemia administration of appropriate compounds and ERG recordings on day 1, 3, 5 or 7 after ischemia). Dark adaption was allowed for 8 hours and then anesthesia was carried out while recording the ERG with dilation of pupils. A stimulus of 0.5 Hz was provided using a strobe 2 cm before the animal's eye. Fifteen continuous recordings were collected at two-second interval and at 10 kHz; their amplitudes were maximized and calculated to find an average by an amplifier P511/regulated power supply RPS 107/stimulator PS22 (Grass-Telefactor). To make comparisons between various groups, the ratio of the b-wave amplitude of one eye (sham or ischemia) to that of the untreated fellow normal eye was measured.

Cresyl Violet Staining

Across all groups, after the rats were sacrificed, they received an intracardial perfusion of physiologic saline. The eyeballs were marked at the 12 o'clock on the cornea using a silk suture and then enucleation was carried out, followed by fixation in 4% paraformaldehyde at 4° C. for 24 hr, dehydration in a graded ethanol series and embedding in paraffin (Tissue-Tek TEC 5; Sakura). Five µm thick sectioned samples were obtained along the vertical meridian. These were subjected to cresyl violet labeling and observed under a light microscope (Leica). Retinal sections were photographed at the same magnifying power and the retinal thickness of various different layers were measured from photographs (Ilford Pan-F plus film, 50 ASA). To quantify the amount of retinal ischemic injury, the whole retinal thicknesses (from the internal limiting membrane, ILM, to retinal pigment epithelium, RPE, layer), and inner retinal thickness (from the ILM to inner nuclear layer, INL) were measured.

RGC Retrograde Staining

Under anesthesia, a 2-cm incision was created in the animal's scalp and two small holes were drilled into the skull as illustrated. Next, injections of 10-µl of 5% fluorogold (Sigma-Aldrich) were carried out using a micropipette at 3.8, 4.0, and 4.2 mm below the surface. The fluorogold was injected 3 days before the animals were sacrificed. Retrieval, fixation, dissection and processing of retinal samples were performed as described previously. The RGC density was calculated as the ratio of the total number of RGCs divided by the total area of the retinal sample.

Immunofluorescence Analysis

After sacrifice of the animals and intracardial perfusion, the rat's eyeballs were enucleated, fixed for 45 min, dehydrated and finally embedded in paraffin as described above. Sampling was carried out 1 day after the sham procedure or induction of retinal ischemia and pre-ischemia/post-ischemia administration of DNL or the vehicle. Each 5 µm retinal section was incubated overnight with primary antibodies, namely either goat anti-ChAT polyclonal antibody (1:100; AB144p; Chemicon), mouse anti-vimentin monoclonal antibody (1:100; V6630; Sigma-Aldrich), or rabbit anti-GFAP polyclonal antibody (Millipore). Next, retinal sections were incubated with an appropriate secondary antibody, either rhodamine-conjugated rabbit anti-goat antibody (1:500; AP106R; Chemicon), or FITC-conjugated goat anti-mouse IgG (1:500; AP124F; Millipore)/anti-rabbit IgG (AP132F; 1:500; Millipore). In parallel, cellular nuclei were labeled using DAPI (Molecular Probes). Finally, retinal sections were examined using a fluorescence microscope (Olympus BX61). To compare the retinal thickness (for Cresyl violet staining) or immunoreactivity levels in the sectioned retinas among different groups, an expert who was masked to the conditions of the sectioned samples was requested to measure the retinal thickness or grade the immunolabeling level of different groups against the control group (sham).

Western Blotting Assays

Retinal/cellular samples were retrieved and sonicated in lysis buffer, namely mammalian protein extraction reagent (MPER; HyCell). Identical quantities of denatured proteins (40 µg/30 µl/well) then underwent sodium dodecyl sulfate polyacrylamide gel electrophoresis (SDS-PAGE; Bio-Rad) as described previously. After separation, the protein bands were transferred to a polyvinylidene difluoride (PVDF)

membrane and then immersed for 12 hours at 4° C. with the following primary antibodies, mouse monoclonal anti-β-actin antibody (AC-15; 1:2,000; ab6276)/anti-HIF-1α antibody (1:200; H1alpha67-ChIP Grade; Abcam Inc.), rabbit polyclonal anti-VEGF antibody (A-20; 1:200; sc-152)/anti-PKM2 antibody (1:500; ab38237), or rabbit monoclonal anti-RBP2 antibody (ab177486; 1:1000; Abcam Inc.). The blots were next immersed with relevant secondary antibody, HRP-conjugated goat anti-rabbit IgG (1:5,000; Santa Cruz Biotechnology Inc.) or goat anti-mouse IgG (1:5,000; sc-2005) at 37° C. for 1 hour. Dilution of primary/secondary antibodies was carried out in 5% fat-free skimmed milk. Finally, the membranes were processed using an enhanced chemiluminescent analysis system (HyCell) and exposed to an X-ray film (Fujifilm). The amount of each protein was then evaluated by scanning densitometry.

Enzyme-Linked Immunosorbent Assay

The level of PLGF was determined using ELISA. One day after ischemia, the retina was separated from the enucleated eye cup, dissociated and then lysed by incubation in MPER (Hycell) for 30 min; the lysate was then centrifuged at 13,000 rpm for another 30 min. The total protein in each sample was determined using a bicinchoninic acid protein kit (Thermo Fisher Scientific). The PLGF levels in the supernatant were measured using a PLGF ELISA kit (CSB-E07400r; Cusabio Life Scince) accordingly. Anti-PLGF antibody had been previously coated onto the microwells. After twice washing each well with 200 µL wash buffer over 15 min, the PLGF in the samples or various concentrations of PLGF standard protein (100 µL) was allowed to bind to the antibodies coated onto the microwells at room temperature for 2 hours on a shaker (75 rpm). After washing each well twice with 200 µL wash buffer (PBST), 100 µL of biotin-conjugated anti-PLGF antibody (diluted in assay buffer: PBST and 0.5% BSA) was added to each well for 1 hour on a shaker (75 rpm), which allowed the binding to the PLGF captured by the coated antibody. After twice washing to remove unbound biotin-conjugated anti-PLGF, 100 µL avidin-HRP (diluted in assay buffer) was added; this bound to the biotin conjugated anti-VEGF-A antibody (75 rpm). Following 1-hour incubation on a shaker, the unbound avidin-HRP was removed by washing twice. Finally, 90 µL of 3,3',5,5'-TMB (100 µM) solution, which was oxidized by HRP, was added to each well for 20 min. The color was then changed to yellow on the addition of 50 µL stop solution (sulfuric acid solution, 100 µM). The maximum absorbance (OD) at 450 nm was detected immediately using a microplate reader (Synergy H1 Hybrid Multi-Mode Reader, Biotek ELx800). The PLGF concentration of each sample was determined by constructing a standard curve using various amounts of PLGF (200, 100, 50, 25, 12.5, 6.25, 3.125 and 0 pg/mL) The instrument was adjusted to zero using a 100 µL sample diluent, which served as the blank. The results were expressed as an OD relative to that of the control group (100%).

Statistical Analysis

Comparisons between two groups were made using the unpaired Student's t-tests. One-way ANOVA was performed to compare three or more independent groups. Following the one-way ANOVA, the Dunnet's test was used to compare the control (e.g. Vehicle+I/R) with all other groups (e.g. DNL1.0+I/R). All results were shown as means±SE. A value of $P<0.05$ was considered significant.

Results

MTT Cell Viability Assay

Figure 1:
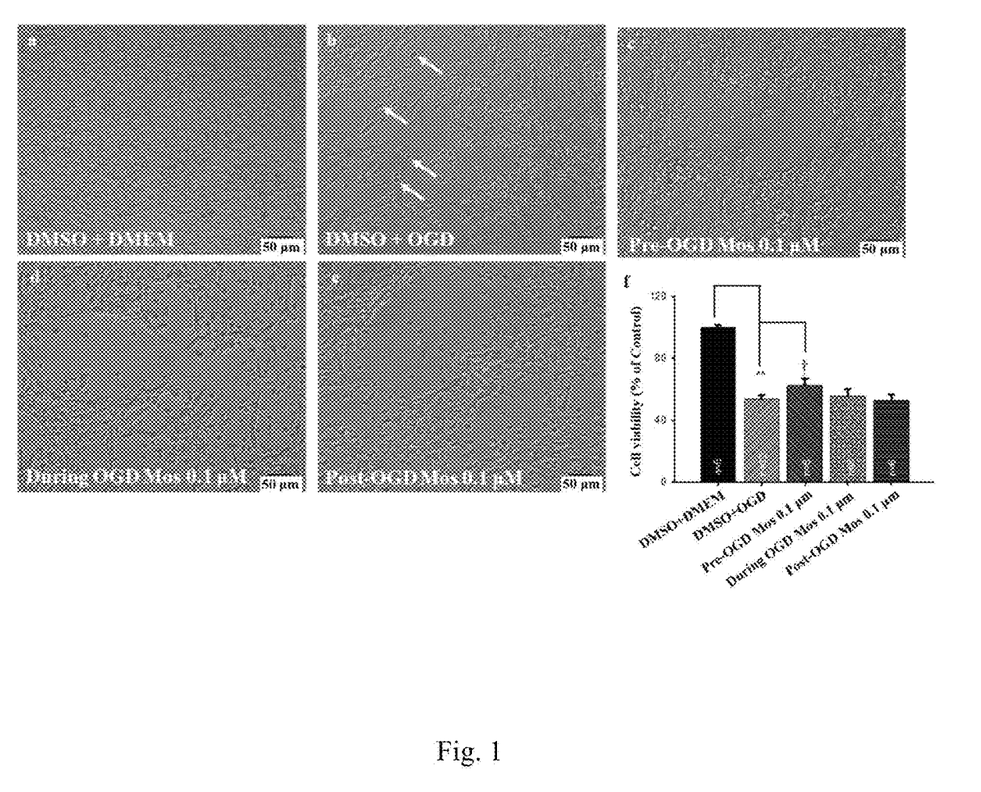

Initially, changes in the cell morphology and the number of RGC-5 cells were examined by light microscopy. The cells cultured in the DMEM with pre-administration of DMSO (DMSO+DMEM; FIG. 1a) had a pyramidal shape and exhibited a characteristic neuronal morphology. In contrast to the DMSO+DMEM group, the cells subjected to OGD and pre-administered with DMSO (DMSO+OGD) were deformed (as indicated by white arrows; FIG. 1b); moreover, there was also a considerable reduction in their cell number. Moscatilin (0.1 µM to 100 µM) was administered to treat the cells subjected to OGD. Moreover, the protective effects of pre-OGD administration of moscatilin on the OGD were demonstrated with greater cell viabilities at 0.1 (62.65±4.35%; n=6) or 1 µM (66.36±9.35%; n=4); however, a cytotoxic effect (a decrease in the cell viability) was shown at 10 (15.43±3.09; n=4) and 100 µM (12.49; n=1). The latter concentrations might be beyond the pharmacological protective levels. Not inconsistently, previous researches had indicated that moscatilin in a time-dependent (1-3 days) and dose-dependent manner (1.25-20 µM) had a cytotoxic effect probably related to its ability to induce a G2 phase arrest in the mitosis at the concentration of 20 or 50 µM as early as 15 h posttreatment. However, the concentrations of moscatilin equal to or less than 1 µM had been proved to be non-toxic and acted as a potent .OH radical scavenger. An investigation into how low concentration of moscatilin (0.1 µM) could increase the cell viability was presently carried out. As compared with the DMSO+OGD group (FIG. 1b), administration of 0.1 µM at 1 hour pre-OGD (FIG. 1c), during OGD (FIG. 1d), or at 1 hour post-OGD (FIG. 1e) were evaluated to demonstrate the extent of cytoprotection against the OGD. The effect of 0.1 µM moscatilin was found to be the greatest when administered at 1 hour pre-OGD (FIG. 1c), then during OGD (FIG. 1d), and none at 1 hour post-OGD (FIG. 1e).

Cell viability was compared against the DMSO+DMEM group (normal control: 100%; n=6); after OGD and pre-administration of DMSO, the cell viability was significantly ($P<0.001$) reduced (53.66±2.67%) in the DMSO+OGD group (FIG. 1f). Furthermore, as compared with the DMSO+OGD group, the administration of 0.1 µM moscatilin 1 hour pre-OGD (FIG. 1f; 62.65±4.35%; P=0.04) resulted in a significant protective effect against the OGD. However, the administration of 0.1 µM moscatilin during OGD (FIG. 1f; 56.03±4.08%; P=0.31), or at 1 hour post-OGD (FIG. 1f; 52.61±4.16%; P=0.41) did not significantly protect cells against the OGD.

The Effect of Moscatilin on the Expression of NDP Relative to β-Actin In Vitro

In order to examine the alterations in vasculogenesis related NDP, representative immunoblotting images and analytical bar chart are presented in FIG. 2 at the top and bottom, respectively. In contrast to the DMSO+DMEM group (normal control: 100%; n=3), pre-OGD administration of vehicle followed by OGD (DMSO+OGD; P<0.001) significantly reduced the amount of NDP to 44.54±3.15%. When the DMSO+OGD group was compared to the pre-OGD Mos 0.1 µm group, there was a significant (P=0.048) rise in the amount of NDP (108.38±29.33%). This elevation in protein expression was the greatest when the moscatilin was administered 1 hour before the OGD, then at 1 h post-OGD (54.36±3.88%), and least during OGD (48.99±9.89%).

The Effect of DNL on ERG b-Wave

Figure 3:
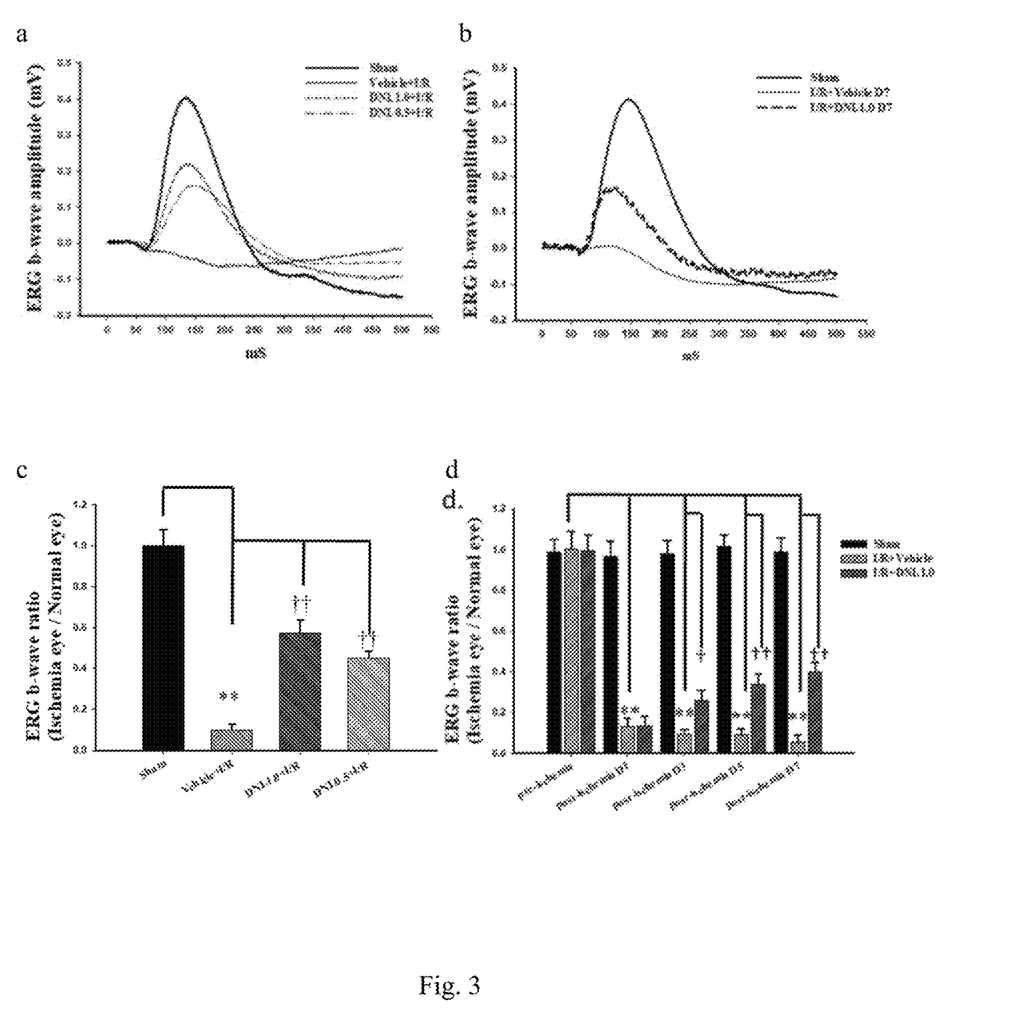

The present invention next examined the retinal electrophysiological functioning. After the sham procedure (Sham, FIG. 3), the ERG b-wave 1 amplitude was measured as 0.41 mV. Following retinal ischemia, there was a drastic reduction in b-wave amplitude and this was not affected by either pre-ischemia or post-ischemia treatment with the vehicle (Vehicle+I/R: 0.03 mV, FIG. 3a; I/R+Vehicle: 0.07 mV, FIG. 3b). However, pre-ischemia (DNL0.5+I/R; DNL1.0+I/R; FIG. 3a) or post-ischemia treatment with DNL (I/R+DNL1.0 D7; FIG. 3b) did alleviate the ischemia-induced b-wave decrease, raising the amplitudes to 0.18, 0.22 and 0.15 mV, respectively. Furthermore, pre-ischemia treatment with DNL dose-dependently attenuated the amplitude decrease.

As shown in FIG. 3c (n=12), compared to the Sham group (1.00±0.08), the b-wave ratio in the Vehicle+I/R group (0.10±0.03) was decreased significantly (P=0.002). Importantly, pre-ischemia treatment with DNL dose-responsively and significantly [DNL1.0+I/R: 0.57±0.06; DNL0.5+I/R: 0.45±0.03 (P<0.001)] mitigated the ischemia-induced b-wave ratio decrease following I/R.

In FIG. 3d (n=10), in comparison with the Sham group, the b-wave ratio was significantly (P<0.001) decreased in the I/R+Vehicle group (day 1: 0.13±0.04; day 3: 0.10±0.02; day 5: 0.09±0.03; day 7: 0.06±0.03). Importantly, post-ischemia administration of DNL (I/R+DNL1.0) significantly [D1: 0.14±0.04; D3: 0.26±0.05 (P=0.02); D5: 0.34±0.05 (P=0.003); D7: 0.40±0.04 (P<0.001)] reduced the ischemia induced b-wave ratio decrease. The pre-ischemia (day 0) b-wave ratios were 1.00±0.09 (I/R+Vehicle) and 1.00±0.08 (I/R+DNL1.0), respectively. A comparison between the ERG b-wave ratios of the Sham group on days 0, 1, 3, 5 and 7 (0.99±0.06, 0.97±0.07, 0.98±0.06, 1.02±0.01 and 0.99±0.07) was made and no significant difference was found.

Figure 4:
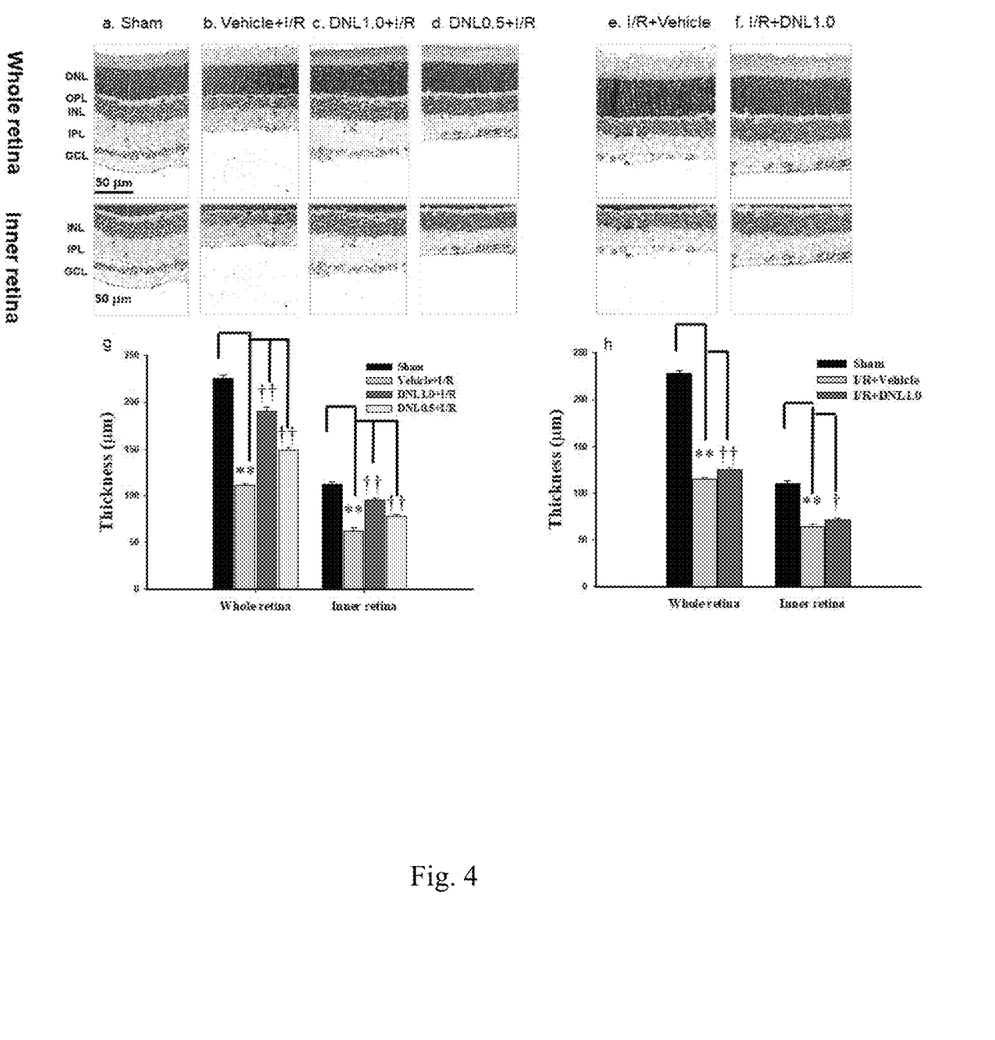

The Effect of DNL on the Thickness of the Retinal Layers Labeled with Cresyl Violet Retinal thickness was assessed by sectioning retinal samples at the same distance (1.5 mm) from disc across various groups (n=10-12; FIG. 4). Compared to retinas receiving the sham procedure (Sham, FIGS. 4a, and 4g: 225.50±3.26 µm for the whole retina, 112.08±2.58 µm for the inner retina), the retinal thicknesses of the animals pre-administered with the vehicle and subjected to I/R (Vehicle+I/R, FIGS. 4b and 4g: 110.83±1.85 µm for the whole retina, 62.50±3.06 µm for the inner retina) were significantly (P<0.001) decreased. Moreover, this decrease was dose-dependently and significantly (P<0.001) counteracted when the animals received I/R and pre9-administration of DNL (DNL1.0+I/R, FIGS. 4c and 4g: 190.08±4.48 µm for the whole retina, 94.92±2.27 µm for the inner retina; DNL0.5+I/R, FIGS. 4d and 4g: 148.58±2.80 µm for the whole retina, 78.25±1.53 µm for the inner retina).

In contrast to the retinas subjected to the sham procedure (Sham, FIG. 4a), the retinal thicknesses of the rats that were given I/R and post-administration of the vehicle (I/R+Vehicle, FIGS. 4e and 4h: 115.00±2.04 µm for the whole retina, 63.92±3.30 µm for the inner retina) were significantly (P<0.001) reduced. Moreover, post-administration of DNL blunted this ischemia-induced reduction significantly [I/R+DNL1.0; FIGS. 4f and 4h: 125.25±2.66 µm for the whole retina (P=0.006); 71.50±1.51 µm for the inner retina (P=0.048)].

The Effect of DNL on the Density of Retrograde Fluorogold Immunolabeled RGCs

Figure 5:
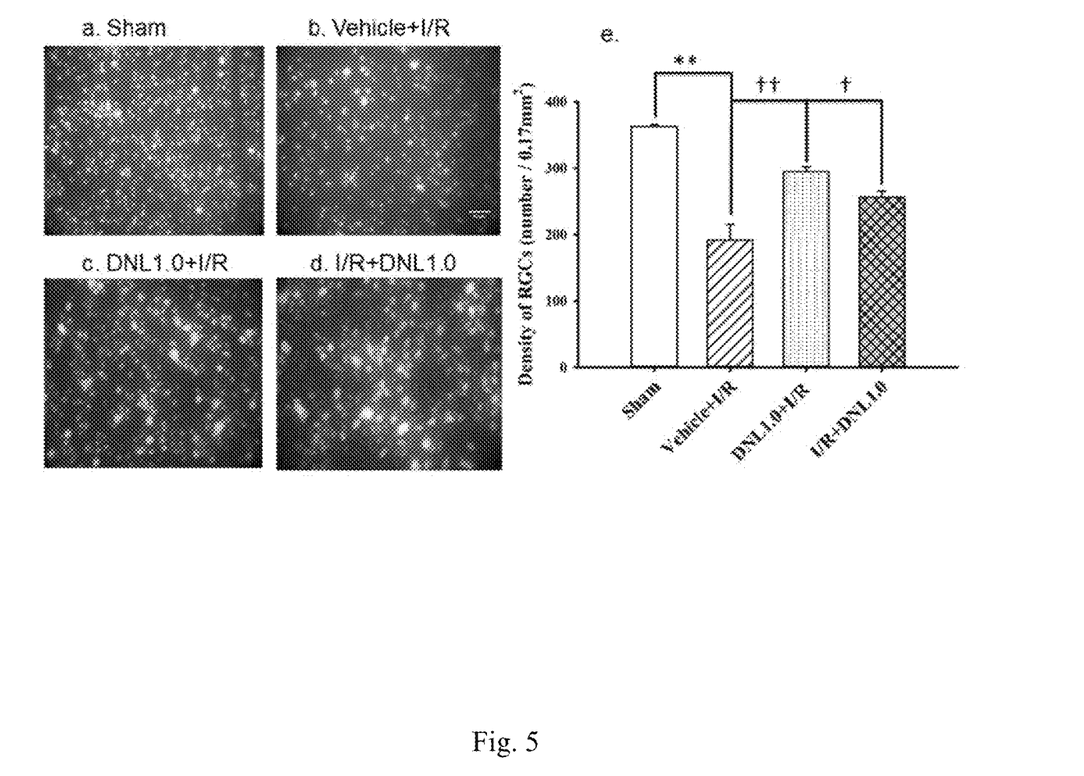

RGC density was assessed (FIG. 5; n=4), and the density of the sham group (Sham, FIGS. 5a and 5e) was 363.23±2.84 cells/field. Compared to the Sham group, there was a significant (P<0.001) reduction in RGC density (192.06±23.53 cells/field) in animals that underwent retinal ischemia and pre-administration of vehicle (Vehicle+I/R, FIGS. 5b and 5e). Furthermore, this decrease was significantly (P=0.006 or 0.045) mitigated when the animals received either retinal ischemia and pre-administration of DNL (DNL1.0+I/R; FIGS. 5c and 5e: 295.15±7.14 cells/field), or post-ischemia administration of DNL (I/R+DNL1.0; FIGS. 5d and 5e: 256.26±9.46 cells/field).

The Effect of DNL Efficacy on ChAT Immunoreactivity

Figure 6:
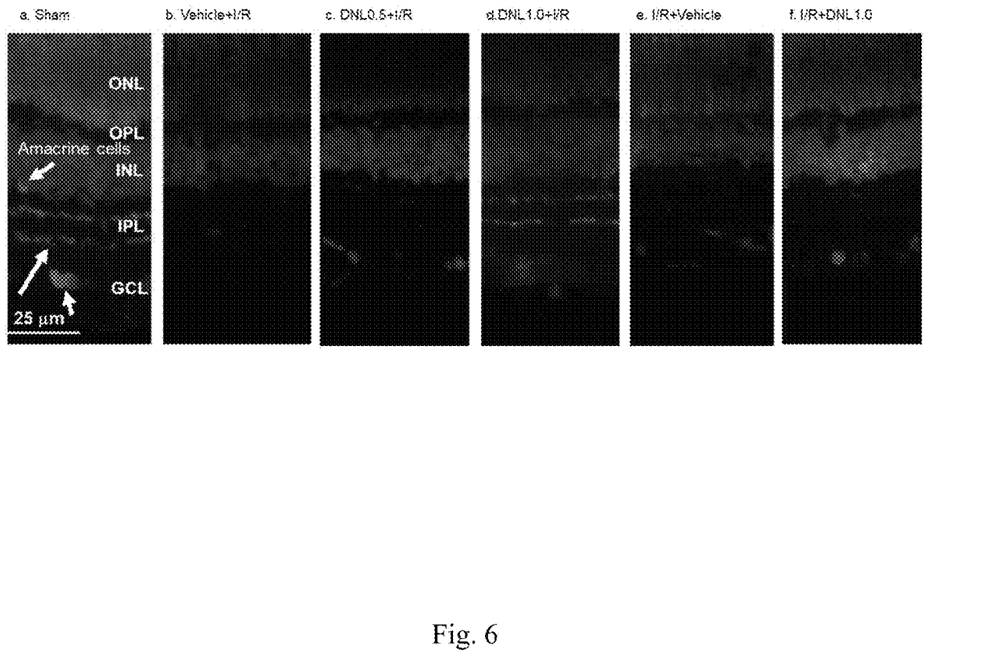

ChAT immunoreactivity in the retina after the sham procedure (Sham; FIG. 6a) showed ChAT (red) immunolabeling of the amacrine cell bodies (short arrows) in the INL and ganglion cell layer (GCL); this also demonstrated two distinct strata (long arrow) within the inner plexiform layer (IPL). In retinas that underwent ischemia and pre-/post-administration of the vehicle (Vehicle+I/R; FIG. 6b; I/R+Vehicle, FIG. 6e), the number of ChAT-immunolabeled amacrine cell bodies were drastically decreased; furthermore, their IPL immunolabeling was considerably reduced. Clinically importantly, these changes were nullified dose-responsively when the ischemic retinas had received pre-administration of DNL (DNL0.5+I/R, FIG. 6c; DNL1.0+I/R, FIG. 15 6d). Additionally, post-administration of DNL (I/R+DNL1.0, FIG. 6f) also obviously mitigated these ischemia-induced changes. Merge images of ChAT and DAPI immunolabelings of cellular nuclei were presented in all images.

The Effect of DNL on Vimentin and GFAP Immunoreactivity

Figure 7:
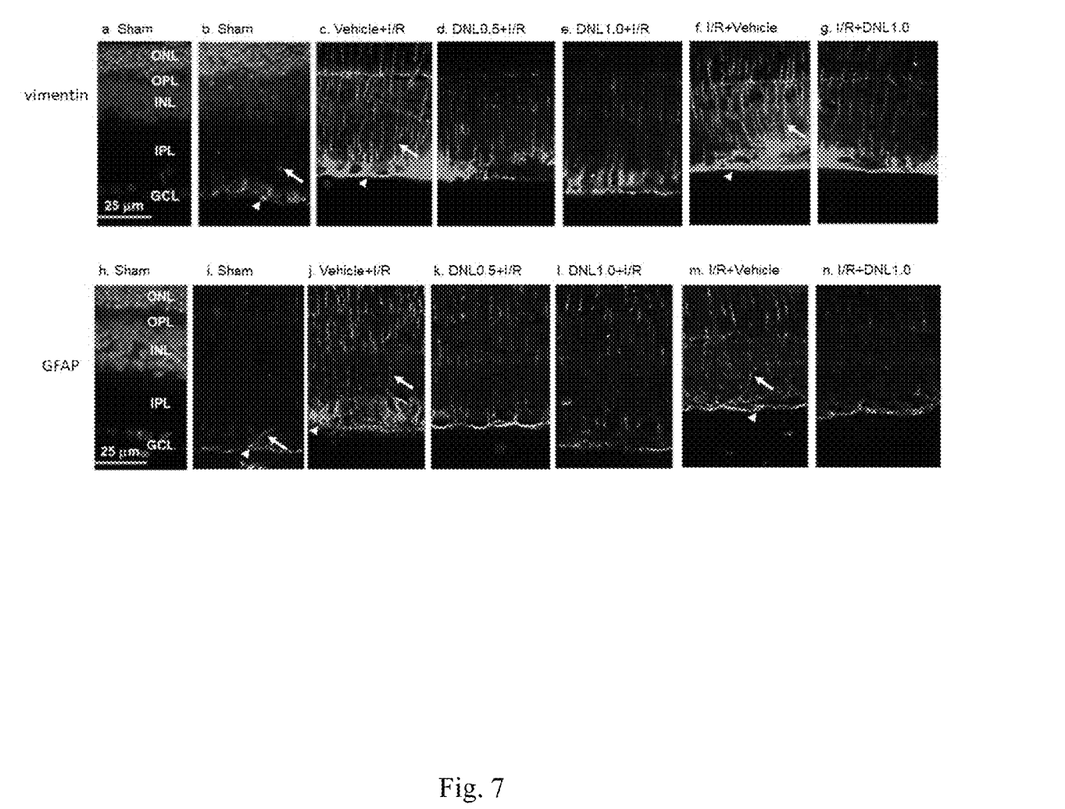

Immunohistochemical investigations were carried out with the aim of investigating the vimentin or GFAP immunoreactivity by using vimentin immunohistochemistry. In the control retina (Sham, FIG. 7b), the Müller cell processes showed vimentin immunolabeling at the end feet (arrow heads; see also FIGS. 7c and 7f) in the GCL and at the processes that extended into the IPL (arrows; see also FIGS. 7c and 7f), INL and ONL. In contrast to the control retina (Sham, FIG. 7b), an increase of the anti-vimentin immunoreactivity was found after retinal I/R and pre-/post-administration of the vehicle (Vehicle+I/R, FIG. 7c; I/R+Vehicle, FIG. 7f). This increase was considerably and dose dependently blunted by pre-administration of DNL (DNL0.5+I/R, FIG. 7d; DNL1.0+I/R, FIG. 7e). Furthermore, post-administration of DNL (I/R+DNL1.0, FIG. 7g) drastically nullified this ischemia-induced change.

GFAP immunohistochemistry. In contrast to the control retina (Sham, FIG. 7i), an increase of the anti-GFAP immunolabeling was observed in the ischemic retina pre/post-administrated with vehicle (Vehicle+I/R, FIG. 7j; I/R+Vehicle, FIG. 7m). Moreover, this change was obviously and dose-responsively reduced when the ischemic retinas were preadministered with DNL (DNL0.5+I/R, FIG. 7k; DNL1.0+I/R, FIG. 7l). Post-administration of DNL (I/R+DNL1.0, FIG. 7n) also obviously reduced this ischemia-induced change. DAPI (blue; FIGS. 7a and 7h) stained cellular nuclei of the Sham retina.

The Effects of DNL1.0 on the Levels of Various Proteins in the Rat Retina

Figure 8:
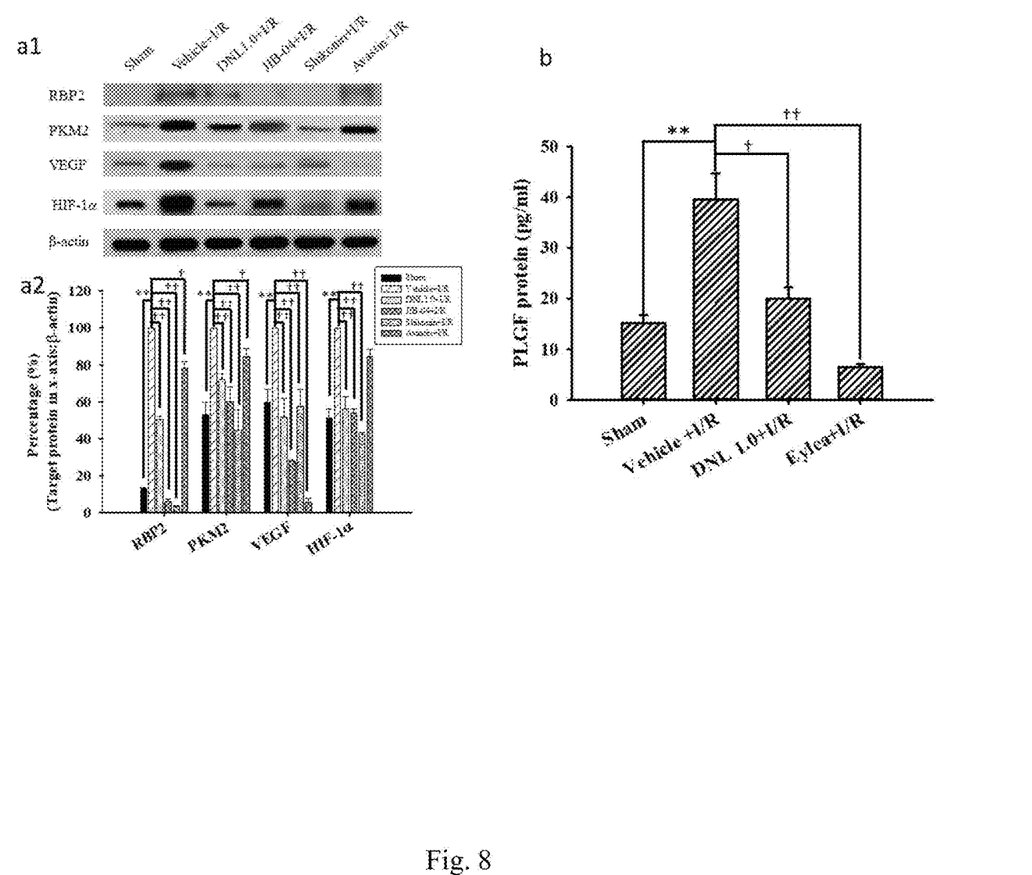

The levels of various proteins in the control retinas (Sham; n=4-10) were measured and the results are shown in FIGS. 8a1 and 8a2 (HIF-1α=51.17±5.14%; VEGF=59.72±6.94%; PKM2=52.93±7.01%; RBP2=12.81±0.55%). In contrast, after I/R and preadministration of the vehicle, a significant (P≤0.001) elevation was observed in the levels of HIF-1α, VEGF, PKM2 and RBP2 (normalized to 100%). Furthermore, this elevation was significantly (P<0.001; HIF-1α=56.08±6.76; VEGF=51.87±9.89; PKM2=71.99±3.05; RBP2=50.64±1.48) inhibited when the ischemic retinas were preadministered with 1.0 g/Kg/day of DNL. Additionally, there was a significant (P≤0.002 except those for avastin) attenuation of the ischemia-induced increase in the levels of HIF-1α [JIB-04=53.98±2.29; shikonin=42.65±0.76; avastin=84 0.61±3.96 (P=0.07)], VEGF (JIB-04=27.82±1.21; shikonin=57.55±9.40; avastin=5.38±2.51), PKM2 [JIB-04=60.36±7.59; shikonin=44.94±10.91; avastin=84.44±4.53 (P=0.01)], and RBP2 (JIB-04=5.83±1.43; shikonin=3.40±0.23; avastin=78.35±3.29 (P=0.02)] after pre-administration of the respective inhibitor/antibody JIB-04 (RBP2 inhibitor), shikonin (PKM2 inhibitor) and avastin (VEGF antibody).

As shown in FIG. 8b (n=4), in contrast to the control retinas (Sham=15.11±1.58 pg/ml), after I/R and pre-administration of vehicle, there was a significant (P=0.004) elevation in the level of PLGF (Vehicle+I/R=39.53±5.25). Moreover, this elevation was significantly (P=0.01 or P<0.001) blunted when the ischemic retinas were pre-administered with DNL (DNL1.0+I/R=19.93±2.24), or anti-PLGF antibody Eylea (Eylea+I/R=6.44±0.60).

Those skilled in the art recognize the foregoing outline as a description of the method for communicating hosted application information. The skilled artisan will recognize that these are illustrative only and that many equivalents are possible.

What is claimed is:

1. A method for treating a subject suffering from a developmental retinal vascular disorder induced by downregulating of norrie disease protein, comprising administering to the subject suffering from the developmental retinal vascular disorder induced by downregulating of norrie disease protein a composition comprising a therapeutically effective amount of dendrobium nobile lindley (DNL), wherein the developmental retinal vascular disorder induced by downregulating of norrie disease protein consists of persistent hyperplastic primary vitreous, norrie disease, familial exudative vitreoretinopathy, and Coats disease.

2. The method of claim 1, wherein the DNL improves the defects in the vasculogenesis to treat the developmental retinal vascular disorder induced by downregulating of norrie disease protein.

3. The method of claim 1, wherein symptoms of the developmental retinal vascular disorder induced by downregulating of norrie disease protein comprise an abnormal development of retinal vessels, retinal ischemia and visual impairments.

4. The method of claim 1, wherein the DNL treats a retinal ischemic damage caused by the developmental retinal vascular disorder induced by downregulating of norrie disease protein.

5. The method of claim 1, wherein the DNL treats the degree of decrease in the retinal thickness caused by the developmental retinal vascular disorder induced by downregulating of norrie disease protein.

6. The method of claim 1, wherein the DNL decreases the level of HIF-1α, RBP2, PKM2 and VEGF.

7. The method of claim 1, wherein the DNL downregulates the level of PLGF and upregulates the level of norrie disease protein to treat the developmental retinal vascular disorder induced by downregulating of norrie disease protein.

8. The method of claim 7, wherein the DNL upregulates the level of norrie disease protein for modulating the Norrin-dependent Wnt signaling pathway to improve an abnormal development of the retinal vessels, thereby treating the developmental retinal vascular disorder induced by downregulating of norrie disease protein.

* * * * *